United States Patent
Kollgard

(10) Patent No.: US 9,671,374 B2
(45) Date of Patent: Jun. 6, 2017

(54) ULTRASOUND PROBE ASSEMBLY, SYSTEM, AND METHOD THAT REDUCE AIR ENTRAPMENT

(71) Applicant: THE BOEING COMPANY, Chicago, IL (US)

(72) Inventor: Jeffrey Reyner Kollgard, Seattle, WA (US)

(73) Assignee: The Boeing Company, Chicago, IL (US)

( * ) Notice: Subject to any disclaimer, the term of this patent is extended or adjusted under 35 U.S.C. 154(b) by 282 days.

(21) Appl. No.: 14/638,282

(22) Filed: Mar. 4, 2015

(65) Prior Publication Data

US 2016/0258909 A1    Sep. 8, 2016

(51) Int. Cl.
*G01N 29/32* (2006.01)
*G01N 29/24* (2006.01)

(52) U.S. Cl.
CPC ..... *G01N 29/2468* (2013.01); *G01N 2291/101* (2013.01); *G01N 2291/2638* (2013.01)

(58) Field of Classification Search
USPC .......................................................... 73/632
See application file for complete search history.

(56) References Cited

U.S. PATENT DOCUMENTS

| | | | |
|---|---|---|---|
| 5,214,251 A * | 5/1993 | Orban ................... | E21B 21/08 181/102 |
| 5,423,220 A * | 6/1995 | Finsterwald .......... | B06B 1/0622 310/322 |
| 7,562,576 B2 | 7/2009 | Fetzer | |
| 8,453,928 B2 | 6/2013 | Melandso | |
| 8,662,395 B2 | 3/2014 | Melandso | |
| 8,914,244 B2 | 12/2014 | Kollgaard | |
| 9,157,896 B2 * | 10/2015 | Ito ........................ | G01N 29/069 |
| 2012/0060612 A1 * | 3/2012 | Kleinert ............... | G01N 29/043 73/632 |

* cited by examiner

*Primary Examiner* — J M Saint Surin
(74) *Attorney, Agent, or Firm* — Joseph M. Butscher; The Small Patent Law Group, LLC

(57) ABSTRACT

An ultrasound probe assembly includes a transducer configured to transmit and receive ultrasound signals in relation to a structure, and a delay line coupled to the transducer. The delay line is configured to change shapes between an uncompressed state and a compressed state. In at least one embodiment, the changing shape of the delay line changes a shape of the ultrasound signals.

22 Claims, 4 Drawing Sheets

ULTRASOUND PROBE ASSEMBLY, SYSTEM, AND METHOD THAT REDUCE AIR ENTRAPMENT

BACKGROUND OF THE DISCLOSURE

Embodiments of the present disclosure generally relate to ultrasound probe assemblies, systems, and methods, and, more particularly, to ultrasound probe assemblies, systems, and methods that are configured to reduce air entrapment, such as would otherwise exist between a delay line and a structure being inspected.

Ultrasound probes are used in various settings. For example, certain ultrasound probes are used to detect damage within various structures, such as portions of aircraft. Lightweight composite materials are used in the aerospace industry for both commercial and military aircraft and other aerospace vehicles, as well as in other industries. Composite structures may be formed using multiple plies or layers of material that may be laminated together to form a high strength structure. The structures may undergo further machining processes during manufacturing and assembly of vehicles (drilling, cutting, countersinking, shimming, fastener removal, etc.), as well as further processes related to flight and ground operations (maintenance, repair, retrofit, or overhaul).

Ultrasound probes may be used to scan structures (such as composite or metal wings, fuselage, and the like of an aircraft) to assess a condition of the structure. For example, if a dent or scuff mark is evident on a portion of an aircraft, a handheld ultrasound probe may be used to determine the existence of sub-surface damage.

A typical ultrasound probe includes a housing that contains a single element transducer. Other known ultrasound probes include multi-element transducers, in which ultrasound elements are arranged in a two-dimensional matrix. The multi-element ultrasound probes are able to produce a spatial C-scan of a small area (such as a dent or hole damage location) with a single placement of the probe. Such probes are commonly referred to as "ultrasonic cameras"

A delay line is secured to a beam transmitting portion of the ultrasound probe to reduce the effects of the ultrasonic near field and eliminate the dead zone caused by the initial ultrasound pulse. Known ultrasound probes include a hard plastic delay line secured to the transducer. Because the delay line is hard and rigid, a liquid coupling agent, such as water, is used between the delay line and the transducer to effectively couple the transducer to the structure.

Typically, delay lines are flat or otherwise conform to a signal-emitting surface of the transducer. If a signal-emitting surface of the transducer is flat, the delay line is also flat. If a signal-emitting surface of the transducer is curved, the curvature of the delay line is typically the same as the surface of the transducer to ensure a constant sound path from the transducer face to the front surface of a structure.

However, during operation, pockets of air may become entrapped between the delay line and the structure that is being examined. The entrapped air, which may be in the form of air bubbles, affects the ability of an ultrasound system to properly display echoes from the structure. The entrapped air may cause image artifacts, reduce image quality, and otherwise hinder accurate analysis of the structure.

Accordingly, a need exists for an assembly, system, and method that eliminates, minimizes, or otherwise reduces air entrapment between an ultrasound probe assembly and a structure that is being examined. Further, a need exists for a method of shaping and focusing a beam beyond the capabilities of single element transducers.

SUMMARY OF THE DISCLOSURE

Certain embodiments of the present disclosure provide an ultrasound probe assembly that may include a transducer configured to transmit and receive ultrasound signals in relation to a structure, and a delay line coupled to the transducer. The delay line is configured to change shapes between an uncompressed state and a compressed state. Compression of the delay line between the uncompressed and compressed states purges air from a space between the delay line and the structure into which the delay line is compressed, and/or provides beam-shaping such as with a single-element transducer. In at least one embodiment, the delay line changing shapes from the uncompressed state to the compressed state causes the ultrasound signals transmitted from the transducer to change shape.

The delay line may be a soft delay line that is configured to conform to an outer surface of the structure as the delay line is compressed into the structure. The delay line may include a transducer-coupling surface that couples to the transducer. The transducer-coupling surface has a first shape in the uncompressed state. The delay line may also include a structure-engaging surface that is configured to engage a surface of the structure. The structure-engaging surface has a second shape in the uncompressed state. The first shape differs from the second shape. In at least one embodiment, the delay line includes a convex outer surface in the uncompressed state, and a flattened outer surface in the compressed state. The delay line may have a constant density throughout in the uncompressed state, and a variable density throughout in the compressed state.

The transducer may include a plurality of transducer elements. Each of the transducer elements may be operatively connected to a separate and distinct lead. A control unit may be operatively connected to the transducer. The control unit may be configured to phase signal pulses to each of the plurality of transducer elements based on the compression of the delay line and/or the change in density of the delay line and corresponding ultrasonic velocity change. In another embodiment, the transducer may include a single transducer element that is curved (such as inwardly curved or concave) to focus an ultrasound wave toward a desired focal point.

The ultrasound probe assembly may also include a retainer positioned around an outer peripheral edge of the delay line. The retainer is configured to maintain the delay line within an imaging envelope of the transducer.

Certain embodiments of the present disclosure provide a method that may include urging an imaging end of an ultrasound probe assembly into a surface of a structure to be inspected, wherein the urging comprises urging a delay line of the ultrasound probe assembly into the surface of the structure, compressing the delay line into a compressed state against the surface of the structure, wherein the compressing operation changes the shape of the delay line, and purging air from the imaging end through the compressing operation.

In at least one embodiment, a single element transducer may be used. The compressing operation may purge air and shape the beam output from the single element transducer.

DETAILED DESCRIPTION OF THE DISCLOSURE

Figure 1:
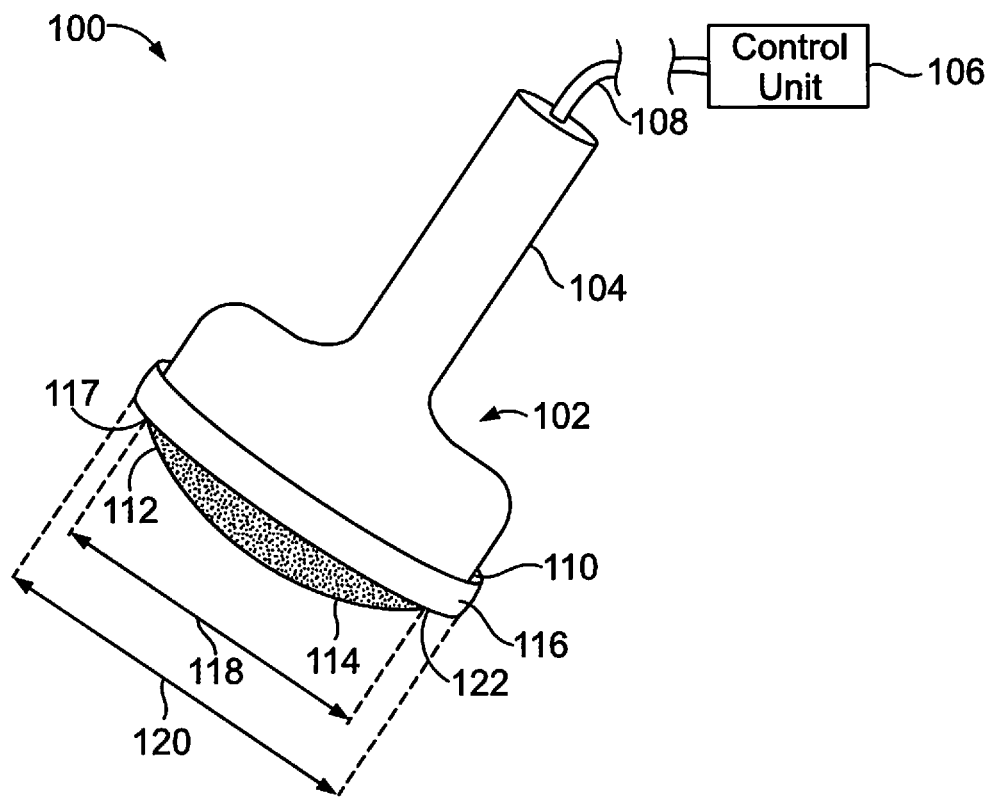
FIG. 1 illustrates a perspective lateral view of an ultrasound probe assembly, according to an embodiment of the present disclosure.

The foregoing summary, as well as the following detailed description of certain embodiments will be better understood when read in conjunction with the appended drawings. As used herein, an element or step recited in the singular and proceeded with the word "a" or "an" should be understood as not excluding plural of the elements or steps, unless such exclusion is explicitly stated. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Certain embodiments of the present disclosure provide an ultrasound probe assembly that may include a delay line that is configured to expel/purge air during operation, and therefore improve image quality. The delay line may be a soft delay line. As used herein, the term soft means flexible, pliable, compressible, and/or conformable. The delay line may include a convex surface that differs from (for example, does not conform to a shape) a transducer-coupling surface of a transducer. In operation, as the delay line is pressed against a structure to be inspected, the convex surface of the delay line that contacts the structure compresses and changes shape. In the compression process, entrapped air between the delay line and the structure escapes along outer edges of the delay line. For example, the entrapped air is squeezed out from the space between the delay line and the structure by the changing shape of the delay line. As such, embodiments of the present disclosure eliminate, minimize, or otherwise reduce air entrapment between an ultrasound probe and a structure being inspected, which, in turn, increases image quality.

Certain embodiments of the present disclosure provide an ultrasound probe assembly that includes a delay line, which may be soft, flexible, and configured to conform to an outer surface of a structure to be inspected. The delay line may include a first surface that conforms to an outer surface of a transducer, and an opposite second surface having a shape that differs from the first surface. For example, the second surface may have a convex shape in an uncompressed or expanded state. Initially, a centerpoint of the convex surface is placed against a structure to be inspected. As the ultrasound probe is pressed against the structure being inspected, the delay line compresses in response. As the delay line compresses, air entrapped between the delay line and the structure is pushed outwardly to the edges of the delay line and escapes. Accordingly, the shape of the delay line eliminates, minimizes, or otherwise reduces air entrapment and thereby increases image quality.

In at least one embodiment, the transducer may include a plurality of individual transducer elements. In at least one other embodiment, the transducer may be a single transducer unit without a plurality of elements.

Certain embodiments of the present disclosure provide an ultrasound probe assembly that may include a transducer configured to transmit and receive ultrasound waves in relation to a structure, and a flexible delay line coupled to the transducer. A surface of the flexible delay line may be convex in an uncompressed or expanded state. As the probe assembly is pressed onto a structure, the shape of the flexible delay line changes to conform or otherwise match a contour of an outer surface of the structure.

The ultrasound probe assembly may also include a retainer, such as a frame, ring, rim, or the like, that circumscribes or is otherwise positioned around an outer periphery of the flexible delay line. The retainer is configured to maintain the flexible delay line within an imaging envelope of the transducer assembly in the compressed state.

Certain embodiments of the present disclosure provide an ultrasound probe assembly including a delay line that eliminates, minimizes, or otherwise reduces nuisance air bubble entrapment beneath an ultrasonic transducer. The delay line may be formed of a soft delay line material, such as rubber, silicone rubber, or the like, having a convex outer surface in an uncompressed state. A retainer may surround an outer peripheral edge of the delay line. When the delay line is pressed into a structure, the shape of the delay line changes, thereby driving air bubbles from the center of the delay line to outer edges, and out of the imaging area underneath the transducer. Pulse timing of transducer array elements may be adjusted based on predicted velocity changes that occur in the delay line as it transitions to a compressed state.

FIG. 1 illustrates a perspective lateral view of an ultrasound probe assembly 100, according to an embodiment of the present disclosure. The ultrasound probe assembly 100 includes a housing 102 connected to a handle 104. The housing 102 securely retains a transducer (hidden from view) that is operatively coupled to a control unit 106 through a cable 108 that routes power and signal lines from the control unit 106 to the transducer. Optionally, the control unit 106 may be contained within the housing 102. The handle 104 allows an individual to grasp and manipulate the ultrasound probe assembly 100 on a surface of a structure to be inspected, for example. Alternatively, the ultrasound probe assembly 100 may not be configured for handheld use. Instead, the housing 102 may be operatively connected to a frame, bracket, shuttle, gantry and/or other such structure that may be operatively connected to one or more actuators that are configured to provide automatic operation of the ultrasound probe assembly 100.

The housing 102 includes an imaging end 110 through which ultrasound signals are transmitted and received. A delay line 112 is secured to the housing 102 at the imaging end 110 and is coupled to the transducer. The delay line 112 may be a soft, flexible, conformable delay line that is configured to change shapes between an uncompressed state (as shown in FIG. 1) to a compressed state as the delay line 112 is urged into a structure. As shown in FIG. 1, in the uncompressed state, the delay line 112 may include a convex shape in which an outer surface 114 is outwardly bowed, curved, or the like. In the uncompressed state, the outer surface 114 may have a different shape than a signal end (for example, the end through which ultrasonic signals are transmitted and received) of the transducer.

The delay line 112 may be a layer of material coupled to the transducer. The delay line 112 may be a soft layer of material (such as rubber, flexible plastic, and/or the like) that may be configured to dampen initial ringing of ultrasound signals transmitted from the transducer. The delay line 112 may be used to dampen or otherwise filter ringing, interference, feedback, or the like from the transducer so that received signals of interest are not obscured, distorted, overwhelmed, or the like.

A retainer 116 is secured to the housing 102 around an outer peripheral edge 117 of the delay line 112. The retainer 116 may be a collar, frame, bracket, detent, rim, or the like that surrounds or circumscribes the outer peripheral edge 117 of the delay line 112. As shown, an outer perimeter 118 of the delay line 112 is less than an inner perimeter 120 of the retainer 116. Accordingly, the retainer 116 defines a perimeter limit past which the delay line 112 may not extend. The retainer 116 maintains the delay line 112 within the perimeter limit. The delay line 112 is prevented from radially extending past the inner perimeter 120 of the retainer 116.

In the uncompressed state, the outer surface 114 of the delay line 112 extends axially past (such as below) a distal edge 122 (for example, a bottom edge, or edge that is configured to abut into a surface of a structure to be inspected) of the retainer 116. Thus, while the retainer 116 controls an outer perimeter or radial shape of the delay line 112, the outer surface 114 extends below the retainer 116 in the uncompressed or expanded state.

In operation, the control unit 106 controls various aspects of the ultrasound probe assembly 100. For example, the control unit 106 is used to control beamforming, phase delays, signal transmission and reception, and the like of the ultrasound probe assembly 100. The control unit 106 may be or include a central processing unit (CPU), which may be in communication with or otherwise include, a memory that stores programs, instructions, and the like that govern operation of the transducer. In short, the control unit 106 may be or include a circuit that includes one or more processors (such as microprocessors, microcontrollers, etc.), one or more memories, and/or the like that are configured to control the beamforming, phase delay, transmission, reception, and the like operations of the ultrasound probe assembly 100.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor capable of executing the functions described herein. Such are exemplary only, and are thus not intended to limit in any way the definition and/or meaning of such terms.

The computer or processor executes a set of instructions that are stored in one or more storage elements (such as one or more memories), in order to process data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The diagrams of embodiments herein may illustrate one or more control or processing units or modules. It is to be understood that the control units or modules represent circuit modules that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the control units or modules may represent processing circuitry such as one or more of a field programmable gate array (FPGA), application specific integrated circuit (ASIC), microprocessor(s), a quantum computing device, and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

Figure 2:
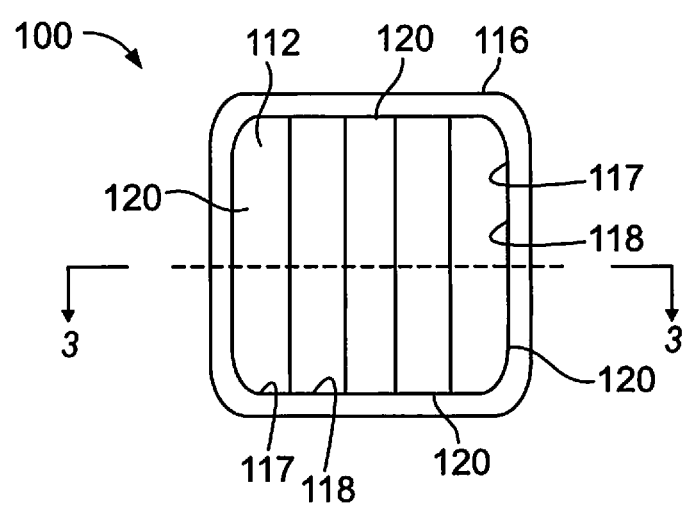
FIG. 2 illustrates a bottom view of an ultrasound probe assembly, according to an embodiment of the present disclosure.

FIG. 2 illustrates a bottom view of the ultrasound probe assembly 100, according to an embodiment of the present disclosure. As shown, the retainer 116 surrounds or circumscribes the outer peripheral edge 117 of the delay line 112. The outer perimeter 118 of the delay line 112 may be bounded by the inner perimeter 120 of the retainer 116.

The retainer 116 may provide a square or rectangular frame around the outer peripheral edge 117 of the delay line 112. Alternatively, the retainer 116 and the delay line 112 may include various other shapes and sizes. For example, an axial cross section of the delay line 112 may be circular, ovoid, elliptical, or the like, while the retainer 116 may have a similar circular or ovoid ring shape. The shapes and sizes of the delay line 112 and the retainer 116 are merely examples, and it is to be understood that various other shapes and sizes may be used.

Figure 3:
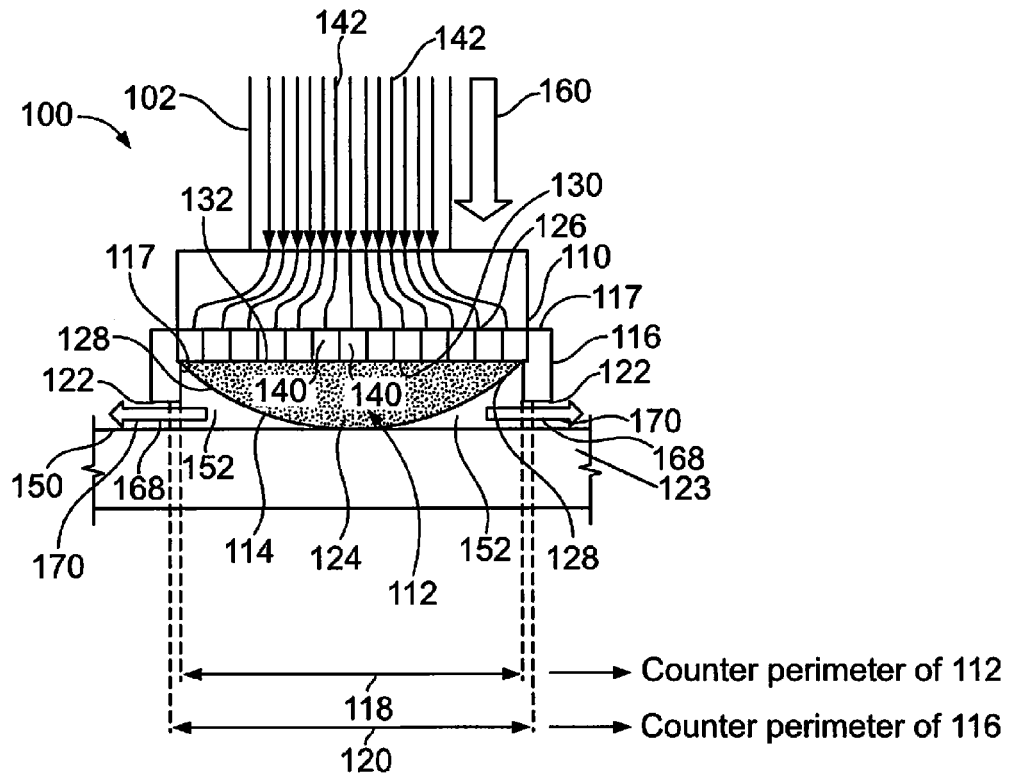
FIG. 3 illustrates an axial cross-sectional view of an ultrasound probe assembly through line 3-3 of FIG. 2 positioned proximate to a structure to be inspected, according to an embodiment of the present disclosure.

FIG. 3 illustrates an axial cross-sectional view of the ultrasound probe assembly 100 through line 3-3 of FIG. 2 positioned proximate to a structure 123 to be inspected, according to an embodiment of the present disclosure. FIG. 3 illustrates the ultrasound probe assembly 100 in an initial inspection position, in which the delay line 112 is in an uncompressed or expanded state. In the uncompressed state, the outer surface 114 of the delay line 112 provides a structure-engaging surface or interface that is convex or semispherical, having an outwardly bowed shape in which a central outer edge 124 is positioned axially further away from a transducer 126 than peripheral edges 128. In contrast, an inner surface 130 of the delay line 112 provides a transducer-coupling surface or interface that conforms to a distal or imaging surface 132 of the transducer 126. As shown, the transducer 126 may be flat. The distal imaging surface 132 of the transducer 126 may be flat. Accordingly, the inner surface 130 of the delay line 112 may be flat due to its coupling to the inner imaging surface 132. In the uncompressed state, however, the shape of the outer surface 114 (for example, the structure-engaging surface) differs from the shape of the inner surface 130. Namely, in the uncompressed state, the outer surface 114 (for example, a convex surface) has a different curvature than the curvature of the inner surface 130 (for example, a flat surface). For example, the inner surface 130 may have no curvature, while the outer surface 114 is outwardly bowed.

The transducer 126 may be a transducer array including a plurality of individual transducer elements 140. More or less transducer elements 140 than shown may be used. Each transducer element 140 is operatively coupled to a respective lead 142 that connects to the control unit 106 (shown in FIG. 1), which may be secured within or outside of the housing 102, as noted above with respect to FIG. 1.

In the initial positioning position, the ultrasound probe assembly 100 is positioned proximate to a surface 150 of the structure 123 to be inspected. The center 124 may abut against or otherwise contact the surface 150. However, the curvature of the outer surface 114 of the delay line 112 curves away from the surface 150 towards the peripheral edges 128. As such, gaps 152 exist between the outer surface 114 and the retainer 116. Air may be positioned within the gaps 152.

As the ultrasound probe assembly 100 is urged downwardly into the surface 150 of the structure 123 the direction of arrow 160, the shape of the delay line 112 changes shape in response to the force of the movement of the ultrasound probe assembly 100. As noted, the delay line 112 is flexible and resilient. Because the delay line 112 is sandwiched between the transducer 126 and the structure 123, with increased urging in the direction of arrow 160, the delay line 112 flattens out, thereby pushing or squeezing air radially outward away from the center 124.

The retainer 116 contains the delay line 112 within an imaging envelope of the transducer 126, thereby preventing the delay line 112 from extending therepast. The imaging envelope is a volume that extends from an imaging end of the transducer. The volume has a cross-sectional area equal to the cross-sectional area of the transducer 126.

As the delay line 112 is compressed into a flat shape, air within the gaps 152 is forced radially outward (for example, pushed, squeezed, or the like by the flattening delay line 112) in the direction of arrows 170 toward the peripheral edges 128 and through spaces 168 between the distal edges 122 of the retainer 116 and the structure 123. Accordingly, air bubbles that are between the structure 123 and the delay line 112 are forced out of the imaging end 110 via the spaces 168 due to the changing shape of the delay line 112 as it is forced into a compressed state. In this manner, air bubbles are purged from the imaging end 110.

In the normal (e.g., expanded, decompressed, or uncompressed) state, the control unit 106 (shown in FIG. 1) may control a time delay of the signal pulses to the transducer elements 140 so that they are sent at the time same. For example, each signal pulse to each individual transducer element 140 may be sent at the same time. However, as the delay line 112 compresses, the control unit 106 may be programmed to delay certain signal pulses based on an expected final compressed shape of the delay line 112. For example, the control unit 106 may be programmed with knowledge of the final compressed shaped of the delay line 112. As the delay line 112 is compressed, the control unit 106 may delay certain signal pulses based on the predetermined final compressed shape of the delay line 112. In at least one other embodiment, the control unit 106 may detect that the shape of the delay line 112 is changing, such as through one or more pressure sensors located on or proximate to the delay line 112 (for example, between the delay line 112 and the transducer 126). The control unit 106 may delay the signal pulses to particular transducer elements 140 in proportion to predetermined ultrasound velocity changes through the delay line 112 as caused by the compression of the delay line 112.

In at least one other embodiment, position or pressure sensors may be operatively coupled between the distal edge 122 of the retainer 116 and the control unit 106. The control unit 106 may detect when the distal edge 122 of the retainer 116 contacts the surface 150 of the structure 123 through signals received from the position or pressure sensors. When the control unit 106 detects that the distal edge 122 contacts the surface 150 (for example, as the retainer 116 bottoms out against the structure 123), the control unit 106 may determine that the delay line 112 is fully compressed, and may change the phasing of signal or excitation signals to the transducer elements 140 accordingly.

Figure 4:
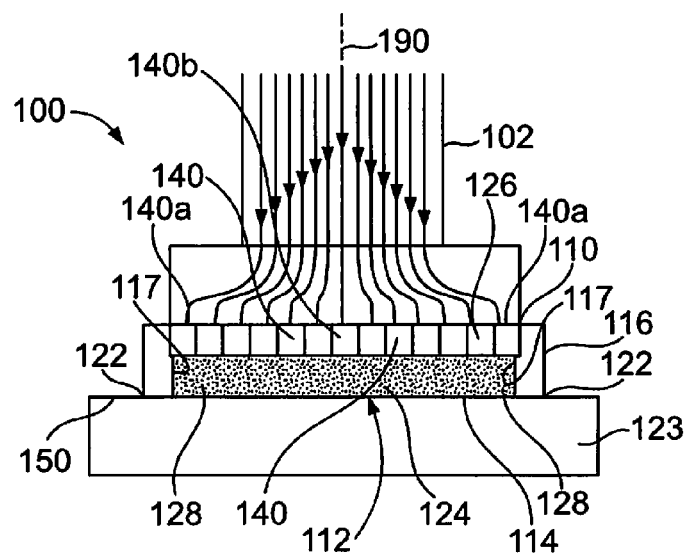
FIG. 4 illustrates an axial cross-sectional view of an ultrasound probe assembly compressed into a structure to be inspected, according to an embodiment of the present disclosure.

FIG. 4 illustrates an axial cross-sectional view of the ultrasound probe assembly 100 compressed into the structure 123 to be inspected, according to an embodiment of the present disclosure. FIG. 4 illustrates the delay line 112 in the compressed state, in which the gaps 152 (shown in FIG. 3) are nonexistent as the space previously occupied by the gaps 152 is occupied by compressed portions of the delay line 112. The distal edges 122 of the retainer abut against the surface 150 of the structure 123, thereby eliminating the spaces 168 (shown in FIG. 3) through which the air bubbles have been expelled.

As the delay line 112 compresses, the shape of the delay line 112 transitions from a convex shape, as shown in FIG. 3, to a flattened, compressed state in which the center 124 is denser than the peripheral edges 128. As shown, the delay line 112 is trapped between the surface 150 of the structure 123, the retainer 116, and the transducer 126. Because the center 124 is outwardly bowed in the uncompressed or expanded state, as the delay line 112 is compressed into the structure 123, the extra material of the center 124 compresses and concentrates more at the center 124 than at the peripheral edges 128, thereby causing the delay line 112 to be denser proximate to the center 124 than at the peripheral edges 128.

The control unit 106 (shown in FIG. 1), having knowledge of the final compressed shape of the delay line 112, is programmed to delay signal pulses to the transducer elements 140 accordingly. For example, because the center 124 of the delay line 112 is denser than the peripheral edges 128 in the compressed state, signals travel through higher density portions faster than the lower density portions. Accordingly, the control unit 106 sends signal pulses to outer transducer elements 140*a* before sending signals to interior transducer elements 140*b*. Pulse signals are more quickly sent from the control unit 106 to the transducer elements 126 the farther the transducer elements 126 are from a central longitudinal axis 190 of the ultrasound probe assembly 100. For example, a pulse signal is sent to a center transducer element 140*b* with a longest delay time, while pulse signals that are sent to the outermost transducer elements 140*a* are sent with the shortest delay time.

As the delay line 112 changes from an uncompressed, expanded, convex shape to a compressed, flat shape, the velocities of ultrasound signals passing through the delay line 112 are altered. In particular, the ultrasound signals travel faster through denser portions of the delay line 112. The control unit 106 accounts and compensates for such changing velocities by phasing the transducer elements 140 (for example, delaying pulse signals to particular transducer elements based different densities of the compressed delay line 112). Excitation or signal pulses may be sent to the central transducer elements 140*b* later than those that are sent to the peripheral transducer elements 140*a*. The net result of such time-delayed phasing of signals provides an undisturbed ultrasound wavefront emitted from the ultrasound probe assembly 100. Further, the changing shape of the delay line 112 as it transitions from the uncompressed state (shown in FIG. 3) to the compressed state (shown in FIG. 4) purges or otherwise expels any air bubbles from a volume between the delay line 112 and the surface 150 of the structure 123 to be inspected.

Figure 5:
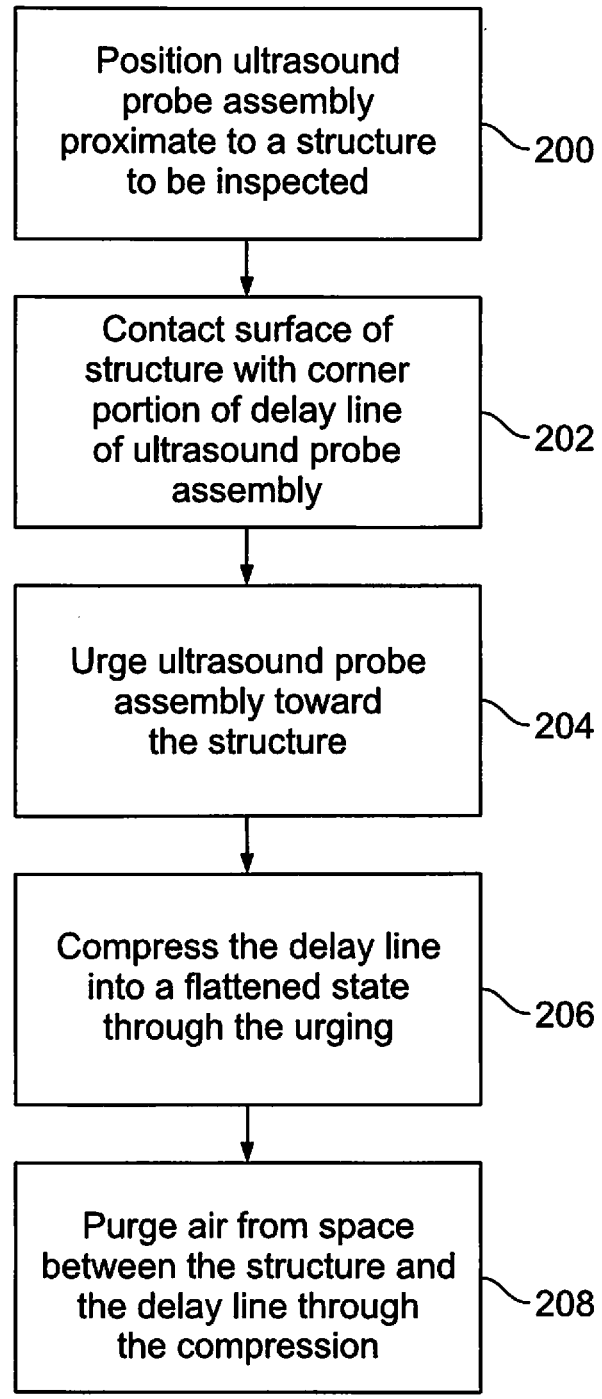
FIG. 5 illustrates a flow chart of a method of expelling air from an imaging end of an ultrasound probe assembly, according to an embodiment of the present disclosure.

FIG. 5 illustrates a flow chart of a method of expelling air from an imaging end of an ultrasound probe assembly, according to an embodiment of the present disclosure. At 200, an ultrasound probe assembly is positioned proximate to a structure to be inspected. At 202, contact between the surface of the structure and a convex portion of a delay line of the ultrasound probe assembly is made. Then, at 204, the ultrasound probe assembly is urged toward the structure, such that the delay line is sandwiched between the surface of the structure and a transducer of the ultrasound probe assembly. At 206, the delay line of the ultrasound probe assembly is compressed into a flattened state through the urging of 204. At 208, air is purged from a space between the structure and the delay line through the compression of the of delay line.

As the delay line is compressed, signal pulses may be phased based on a density of the delay line at various areas. For example, signal pulses that excite transducer elements may be delivered to transducer elements proximate to central, dense portions of the compressed delay line at a later time than signal pulses are delivered to transducer elements that are proximate to less dense portion of the compressed delay line.

Figure 6:
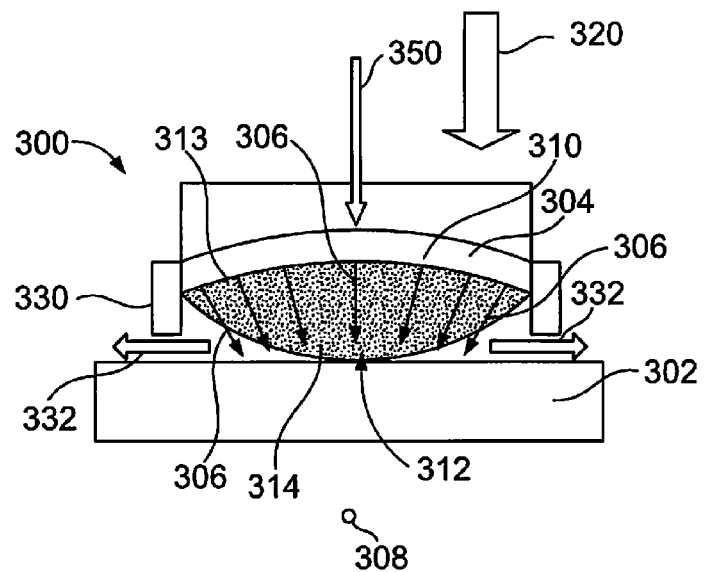
FIG. 6 illustrates an axial cross-sectional view of an ultrasound probe assembly positioned proximate to a structure to be inspected, according to an embodiment of the present disclosure.

FIG. 6 illustrates an axial cross-sectional view of an ultrasound probe assembly 300 positioned proximate to a structure 302 to be inspected, according to an embodiment of the present disclosure. The probe assembly 300 is similar to the probe assembly 100 (shown and described with respect to FIGS. 1-4), except that the probe assembly 300 includes a single element transducer 304 that transmits ultrasound signals 306 toward a focal point 308. As such, the transducer 304 may include an inwardly-bowed structure having a concave surface 310.

A delay line 312 is coupled to the concave surface 310. The delay line 312 may include a transducer-coupling surface 313 that is convex, having a contour that complements and is reciprocal to the concave surface 310. The delay line 312 may also include a structure-engaging surface 314 that is also convex. The transducer-coupling surface 313 and the structure-engaging surface 314 include outwardly bowed surfaces that extend in opposite directions in the uncompressed or expanded state, as shown in FIG. 6.

In operation, as the ultrasound probe assembly 300 is urged into the structure 302 in the direction of arrow 320, air is purged from the space between the delay line 312 and the structure 302 underneath distal edges of a retainer 330 in the directions of arrows 332, as described above. A single lead 350 connects the transducer 304 to a control unit, such as the control unit 106 (shown in FIG. 1). The ultrasound probe assembly 300 may not phase signal pulses to the transducer 304. Instead, because only a single transducer element is used (for example, the transducer 304 itself), a single signal pulse is conveyed to the transducer 304 through the lead 350.

The curvature of the transducer 304 is proportional to a density of the delay line 312 in the compressed state. That is, with knowledge of the density of the delay line 312 in a fully compressed state, the transducer 304 is curved accordingly to ensure that the ultrasound signals 306 are directed toward the focal point 308.

Notably, the height of the retainer 330 may control the compression of the delay line 312. For example, the delay line 312 may not be compressed to a depth that exceeds the height of the retainer 330. When the retainer 330 bottoms out against the surface of the structure 302, the retainer 330 braces the ultrasound probe assembly 300 against the structure, such that the delay line 312 may not be compressed further between the transducer 304 and the structure 302. The retainers of any of the embodiments of the present disclosure may control compression of the delay line in such a manner.

Because the compression of the delay line may be limited by the retainer 330, a maximum amount of compression of the delay line 312 may be known. Knowledge of the maximum amount of compression of the delay line 312 may be used to determine the curvature of the transducer 304.

As shown and described, certain embodiments of the present disclosure provide a delay line, such as the delay line 312, that may change shape and thereby shape an ultrasound beam generated by a single element transducer, such as the transducer 304. On a composite part radius, for example, the delay line may be contoured such that compression defocuses the ultrasound beam and allows it to impinge upon and pass into a structure at angles near normal to all surfaces. On a flat metallic or composite part, for example, in which increased sensitivity may be desired at a certain depth, the delay line may be contoured to provide additional focusing.

Figure 7:
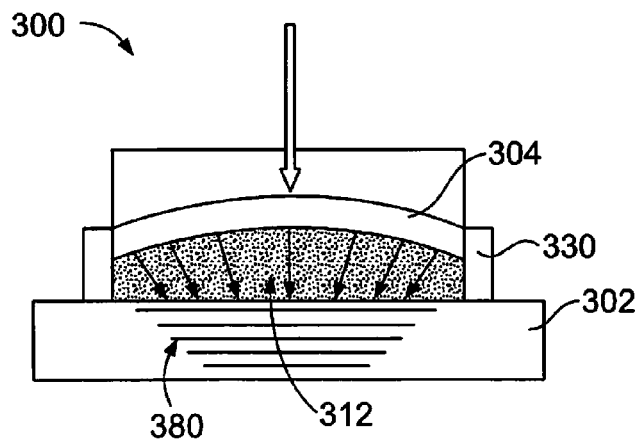
FIG. 7 illustrates an axial cross-sectional view of an ultrasound probe assembly compressed into a structure to be inspected, according to an embodiment of the present disclosure.

FIG. 7 illustrates an axial cross-sectional view of the ultrasound probe assembly 300 compressed into the structure 302 to be inspected, according to an embodiment of the present disclosure. The delay line 312 is shown in the compressed state. The compression of the delay line 312 may be limited by the retainer 330, as described above. The curvature of the transducer 304 may shape and focus an ultrasound beam 380 toward a focal point.

Figure 8:
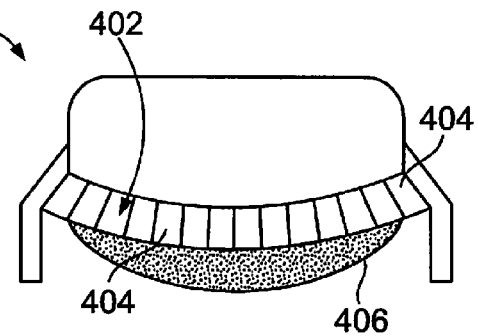
FIG. 8 illustrates an axial cross-sectional view of an ultrasound probe assembly, according to an embodiment of the present disclosure.

FIG. 8 illustrates an axial cross-sectional view of an ultrasound probe assembly 400, according to an embodiment of the present disclosure. The ultrasound probe assembly 400 is similar to those described above, except that the ultrasound probe assembly 400 may include an outwardly-bowed curved transducer 402 having a plurality of transducer elements 404, each of which may include an outer curvature. A delay line 406 is coupled to the transducer 402, and is configured to change shapes between the uncompressed state and a compressed state, as described above.

In short, embodiments of the present disclosure may be used with various types of ultrasound transducers. For example, a delay line that is configured to change shapes may be used with a transducer having a single element, or multiple transducer elements. Further, the transducer may be a flat, linear transducer. Optionally, the transducer may be curved to focus a beam towards a desired focal point when the delay line is compressed. Alternatively, the transducer may be outwardly curved or bowed, as shown in FIG. 8, for example, and the delay line may be shape and configured to focus or de-focus ultrasound signals in parts.

The transducer may be a single element with curvature in one axis, or an array having multiple elements. In at least one other embodiment, the transducer may be a single element with curvature in two axes, or an array having multiple elements. Alternatively, embodiments of the present disclosure may be used with three-dimensional transducer elements or arrays.

Referring to FIGS. 1-8, embodiments of the present disclosure provide an ultrasound probe assembly, system, and assembly that eliminates, minimizes, or otherwise reduces air entrapment between an ultrasound probe assembly and a structure that is being examined. Embodiments of the present disclosure provide an ultrasound probe assembly that may include a delay line that is coupled to a transducer. The delay line may be a soft delay line, such as formed of rubber, pliable plastic, or the like, that is configured to change shapes between an uncompressed or expanded state and a compressed state. As the delay line is compressed, air between the delay line and a structure to be inspected is purged, thereby eliminating, minimizing, or otherwise reducing potential image distortion caused by air. Embodiments of the present disclosure also provide a delay line that may be compressed to shape an ultrasound beam (focusing or de-focusing effects) to compensate for concave or convex part geometries.

Embodiments of the present disclosure may also include a retainer positioned around a periphery of the delay line. The retainer may limit an amount of compression of the delay line by providing a hard stop in relation to the structure to be inspected. Alternatively, the ultrasound probe assembly may not include the retainer.

While various spatial and directional terms, such as top, bottom, lower, mid, lateral, horizontal, vertical, front and the like may be used to describe embodiments of the present disclosure, it is understood that such terms are merely used with respect to the orientations shown in the drawings. The orientations may be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments of the disclosure without departing from their scope.

While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. An ultrasound probe assembly, comprising:
    a transducer configured to transmit and receive ultrasound signals in relation to a structure; and
    a delay line coupled to the transducer, wherein the delay line is configured to change shapes between an uncompressed state and a compressed state, wherein the delay line comprises:
        a transducer-coupling surface that couples to the transducer, wherein the transducer-coupling surface has a first shape in the uncompressed state; and
        a structure-engaging surface that is configured to engage a surface of the structure, wherein the structure-engaging surface has a second shape in the uncompressed state, wherein the first shape differs from the second shape.

2. The ultrasound probe assembly of claim 1, wherein compression of the delay line between the uncompressed and compressed states purges air from a space between the delay line and the structure into which the delay line is compressed.

3. The ultrasound probe assembly of claim 1, wherein the delay line is a soft delay line that is configured to conform to an outer surface of the structure as the delay line is compressed into the structure.

4. The ultrasound probe assembly of claim 1, wherein the delay line includes a convex outer surface in the uncompressed state, and wherein the delay line includes a flattened outer surface in the compressed state.

5. The ultrasound probe assembly of claim 1, wherein the delay line has a constant density throughout in the uncompressed state, and wherein the delay line has a variable density throughout in the compressed state.

6. The ultrasound probe assembly of claim 1, wherein the transducer comprises a plurality of transducer elements, wherein each of the transducer elements is operatively connected to a separate and distinct lead.

7. The ultrasound probe assembly of claim 6, further comprising a control unit operatively connected to the transducer, wherein the control unit is configured to phase signal pulses to each of the plurality of transducer elements based on the compression of the delay line.

8. The ultrasound probe assembly of claim 1, wherein the transducer comprises a single transducer element that is curved to focus an ultrasound wave toward a desired focal point.

9. The ultrasound probe assembly of claim 1, wherein the delay line changing shapes from the uncompressed state to the compressed state causes the ultrasound signals transmitted from the transducer to change shape.

10. The ultrasound probe assembly of claim 1, further comprising a retainer positioned around an outer peripheral edge of the delay line, wherein the retainer is configured to maintain the delay line within an imaging envelope of the transducer.

11. A method comprising:
coupling a transducer-coupling surface of a delay line to a transducer of an ultrasound probe assembly, wherein the transducer-coupling surface has a first shape in an uncompressed state;
urging an imaging end of the ultrasound probe assembly into a surface of a structure to be inspected, wherein the urging comprises urging the delay line of the ultrasound probe assembly into the surface of the structure;
compressing the delay line into a compressed state against the surface of the structure, wherein the compressing operation changes the shape of the delay line;
purging air from the imaging end through the compressing operation; and
engaging the surface of the structure with a structure-engaging surface of the delay line during the urging, compression, and purging operations, wherein the structure-engaging surface has a second shape in the uncompressed state, wherein the first shape differs from the second shape.

12. The method of claim 11, wherein the compressing operation purges the air from a space between the delay line and the structure into which the delay line is compressed.

13. The method of claim 11, further comprising changing a shape of at least one ultrasound signal transmitted from the transducer through the compressing operation.

14. The method of claim 11, wherein the delay line includes a convex outer surface in the uncompressed state, and wherein the delay line includes a flattened outer surface in the compressed state.

15. The method of claim 11, wherein the delay line has a constant density throughout in an uncompressed state, and wherein the delay line has a variable density throughout in the compressed state.

16. The method of claim 11, further comprising phasing signal pulses to each of a plurality of transducer elements based on the compression of the delay line.

17. The method of claim 11, further comprising:
positioning a retainer around an outer peripheral edge of the delay line; and
using the retainer to maintain the delay line within an imaging envelope of the transducer.

18. An ultrasound probe assembly, comprising:
a transducer configured to transmit and receive ultrasound signals in relation to a structure;
a soft delay line coupled to the transducer, wherein the delay line is configured to change shapes between an uncompressed state and a compressed state, wherein compression of the delay line between the uncompressed and compressed states purges air from a space between the delay line and the structure into which the delay line is compressed, wherein the delay line is configured to conform to an outer surface of the structure as the delay line is compressed into the structure, wherein the delay line has a constant density throughout in the uncompressed state, wherein the delay line has a variable density throughout in the compressed state, and wherein the delay line comprises: (a) a transducer-coupling surface that couples to the transducer, wherein the transducer-coupling surface has a first shape in the uncompressed state, and (b) a structure-engaging surface that is configured to engage a surface of the structure, wherein the structure-engaging surface has a second shape in the uncompressed state, wherein the first shape differs from the second shape, wherein the soft delay line changing shapes from the uncompressed state to the compressed state causes the ultrasound signals transmitted from the transducer to change shape;
a retainer positioned around an outer peripheral edge of the delay line, wherein the retainer is configured to maintain the delay line within an imaging envelope of the transducer during the uncompressed and compressed states; and
a control unit operatively connected to the transducer, wherein the control unit is configured to phase signal pulses to each of the plurality of transducer elements based on the compression of the delay line.

19. A method comprising:
urging an imaging end of an ultrasound probe assembly into a surface of a structure to be inspected, wherein the urging comprises urging a delay line of the ultrasound probe assembly into the surface of the structure, wherein the delay line includes a convex outer surface in the uncompressed state;
compressing the delay line into a compressed state against the surface of the structure, wherein the compressing operation changes the shape of the delay line, wherein the delay line includes a flattened outer surface in the compressed state; and
purging air from the imaging end through the compressing operation.

20. A method comprising:
urging an imaging end of an ultrasound probe assembly into a surface of a structure to be inspected, wherein the urging comprises urging a delay line of the ultrasound probe assembly into the surface of the structure wherein the delay line has a constant density throughout in an uncompressed state;
compressing the delay line into a compressed state against the surface of the structure, wherein the compressing operation changes the shape of the delay line, wherein the delay line has a variable density throughout in the compressed state; and
purging air from the imaging end through the compressing operation.

21. A method comprising:
urging an imaging end of an ultrasound probe assembly into a surface of a structure to be inspected, wherein the urging comprises urging a delay line of the ultrasound probe assembly into the surface of the structure;

compressing the delay line into a compressed state against the surface of the structure, wherein the compressing operation changes the shape of the delay line;

purging air from the imaging end through the compressing operation; and phasing signal pulses to each of a plurality of transducer elements based on the compression of the delay line.

22. A method comprising:

positioning a retainer around an outer peripheral edge of a delay line of an ultrasound probe assembly;

using the retainer to maintain the delay line with an imaging envelope of a transducer of the ultrasound probe assembly;

urging an imaging end of the ultrasound probe assembly into a surface of a structure to be inspected, wherein the urging comprises urging the delay line of the ultrasound probe assembly into the surface of the structure;

compressing the delay line into a compressed state against the surface of the structure, wherein the compressing operation changes the shape of the delay line; and purging air from the imaging end through the compressing operation.

\* \* \* \* \*